(12) United States Patent (10) Patent No.: US 8,685,035 B2
de Villiers et al. (45) Date of Patent: Apr. 1, 2014

(54) INTERVERTEBRAL PROSTHESIS PLACEMENT INSTRUMENT

(75) Inventors: Malan de Villiers, Gauteng (ZA); Ulrich Reinhard Hähnle, Saxonwold (ZA)

(73) Assignee: SpinalMotion, Inc., Mountain View, CA (US)

( * ) Notice: Subject to any disclaimer, the term of this patent is extended or adjusted under 35 U.S.C. 154(b) by 2188 days.

(21) Appl. No.: 11/187,403

(22) Filed: Jul. 21, 2005

(65) Prior Publication Data

US 2006/0030862 A1 Feb. 9, 2006

Related U.S. Application Data

(63) Continuation of application No. PCT/IB2004/000170, filed on Jan. 26, 2004.

(30) Foreign Application Priority Data

Jan. 31, 2003 (ZA) .................................. 2003/0874

(51) Int. Cl.
*A61B 17/58* (2006.01)
*A61B 17/60* (2006.01)
*A61F 2/00* (2006.01)
*A61B 1/32* (2006.01)

(52) U.S. Cl.
USPC ............................................ 606/99; 600/219

(58) Field of Classification Search
USPC .............................. 606/99, 86 R, 53; 600/219
See application file for complete search history.

(56) References Cited

U.S. PATENT DOCUMENTS

| 3,486,505 A | 12/1969 | Morrison |
| 4,566,466 A | 1/1986 | Ripple et al. |
| 4,759,766 A | 7/1988 | Buettner-Janz et al. |
| 4,759,769 A | 7/1988 | Hedman et al. |
| 4,834,757 A | 5/1989 | Brantigan |
| 4,863,477 A | 9/1989 | Monson |
| 4,997,432 A * | 3/1991 | Keller .......................... 623/17.11 |

(Continued)

FOREIGN PATENT DOCUMENTS

DE 3023353 A1 4/1981
DE 10035182 A1 * 2/2002

(Continued)

OTHER PUBLICATIONS

Karin Buttner-Janz, The Development of the Artificial Disc, Introduction, 1989, pp. 1-18, Library of Congress Catalogue No. 92-75582, ISBN 0-9635430-0-8.

(Continued)

*Primary Examiner* — David Bates
(74) *Attorney, Agent, or Firm* — Wilson Sonsini Goodrich & Rosati

(57) ABSTRACT

The invention concerns an intervertebral prosthesis placement instrument which can be used to facilitate accurate positioning of a spinal disc prosthesis between adjacent spinal vertebrae. The instrument (10) has opposed jaws 12 formed with tips (24) that are shaped for insertion between the vertebrae. The jaws can be moved apart from one another to distract the vertebrae, allowing the prosthesis to enter between the vertebrae. The jaws also have opposed surfaces which are shaped to embrace the prosthesis between them and to guide the prosthesis into position.

26 Claims, 1 Drawing Sheet

(56) References Cited

U.S. PATENT DOCUMENTS

| | | |
|---|---|---|
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,314,477 A | 5/1994 | Marnay |
| 5,370,697 A | 3/1995 | Buttner-Janz et al. |
| 5,401,269 A | 3/1995 | Buttner-Janz et al. |
| 5,415,704 A | 5/1995 | Davidson |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Buttner-Janz |
| 5,674,296 A | 10/1997 | Bryan et al. |
| 5,676,701 A | 10/1997 | Yuan et al. |
| 5,676,702 A | 10/1997 | Ratron |
| 5,702,450 A | 12/1997 | Bisserie |
| 5,728,159 A | 3/1998 | Stroever et al. |
| 5,797,909 A | 8/1998 | Michelson |
| 5,824,094 A | 10/1998 | Serhan et al. |
| 5,836,948 A * | 11/1998 | Zucherman et al. .......... 606/249 |
| 5,865,846 A | 2/1999 | Bryan et al. |
| 5,888,226 A | 3/1999 | Rogozinski |
| 5,899,901 A | 5/1999 | Middleton |
| 5,899,911 A | 5/1999 | Carter |
| 5,928,284 A | 7/1999 | Mehdizadeh |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,763 A | 3/2000 | Shelokov |
| 6,080,155 A | 6/2000 | Michelson |
| 6,083,228 A | 7/2000 | Michelson |
| 6,096,038 A | 8/2000 | Michelson |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,176,881 B1 | 1/2001 | Schar et al. |
| 6,224,595 B1 | 5/2001 | Michelson |
| 6,235,030 B1 | 5/2001 | Zucherman et al. |
| 6,261,296 B1 | 7/2001 | Aebi et al. |
| 6,264,695 B1 | 7/2001 | Stoy |
| 6,315,797 B1 | 11/2001 | Middleton |
| 6,322,567 B1 | 11/2001 | Mittelstadt et al. |
| 6,348,071 B1 | 2/2002 | Steffee et al. |
| 6,368,350 B1 | 4/2002 | Erickson et al. |
| 6,395,032 B1 | 5/2002 | Gauchet |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 * | 7/2003 | Fuss et al. ........................ 606/99 |
| 6,607,558 B2 | 8/2003 | Karus |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,652,533 B2 | 11/2003 | O'Neil |
| 6,666,866 B2 | 12/2003 | Martz et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,825 B2 | 3/2004 | Aebi et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,740,118 B2 | 5/2004 | Eisermann et al. |
| 6,740,119 B2 | 5/2004 | Ralph et al. |
| 6,755,841 B2 | 6/2004 | Fraser et al. |
| 6,770,095 B2 | 8/2004 | Grinberg et al. |
| 6,814,737 B2 | 11/2004 | Cauthan |
| 6,821,298 B1 | 11/2004 | Jackson |
| 6,830,570 B1 * | 12/2004 | Frey et al. .................. 623/17.16 |
| 6,875,213 B2 | 4/2005 | Michelson |
| 6,896,680 B2 | 5/2005 | Michelson |
| 6,936,071 B1 | 8/2005 | Marnay et al. |
| 6,936,132 B2 | 8/2005 | Topolnitsky |
| 6,966,929 B2 | 11/2005 | Mitchell |
| 6,994,727 B2 | 2/2006 | Khandkar et al. |
| 7,025,787 B2 | 4/2006 | Bryan et al. |
| 7,056,344 B2 | 6/2006 | Huppert et al. |
| 7,060,073 B2 | 6/2006 | Frey et al. |
| 7,083,649 B2 * | 8/2006 | Zucherman et al. ........ 623/17.11 |
| 7,179,294 B2 | 2/2007 | Eisermann et al. |
| 7,182,784 B2 | 2/2007 | Evans et al. |
| 7,270,679 B2 | 9/2007 | Istephanous et al. |
| 7,442,211 B2 | 10/2008 | de Villiers et al. |
| 2001/0016773 A1 | 8/2001 | Serhan et al. |
| 2001/0029377 A1 | 10/2001 | Aebi et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0045939 A1 | 3/2003 | Casutt |
| 2003/0074076 A1 | 4/2003 | Ferree et al. |
| 2003/0100951 A1 | 5/2003 | Serhan et al. |
| 2003/0130662 A1 | 7/2003 | Michelson |
| 2003/0135277 A1 | 7/2003 | Bryan et al. |
| 2003/0187448 A1 | 10/2003 | Michelson |
| 2003/0191536 A1 | 10/2003 | Ferree |
| 2003/0195517 A1 | 10/2003 | Michelson |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2004/0002761 A1 | 1/2004 | Rogers et al. |
| 2004/0024407 A1 | 2/2004 | Ralph |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0059318 A1 | 3/2004 | Zhang et al. |
| 2004/0073307 A1 | 4/2004 | Keller |
| 2004/0073312 A1 | 4/2004 | Eisermann et al. |
| 2004/0098131 A1 | 5/2004 | Bryan et al. |
| 2004/0143270 A1 | 7/2004 | Zucherman et al. |
| 2004/0176843 A1 | 9/2004 | Zubok et al. |
| 2004/0186569 A1 | 9/2004 | Berry |

(56) References Cited

U.S. PATENT DOCUMENTS

| | | |
|---|---|---|
| 2004/0215342 A1 | 10/2004 | Suddaby |
| 2004/0225295 A1 | 11/2004 | Zubok et al. |
| 2005/0015094 A1 | 1/2005 | Keller |
| 2005/0015095 A1 | 1/2005 | Keller |
| 2005/0021145 A1 | 1/2005 | de Villiers et al. |
| 2005/0021146 A1 | 1/2005 | de Villiers et al. |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0149189 A1 | 7/2005 | Mokhtar et al. |
| 2005/0165408 A1 | 7/2005 | Puno et al. |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0251262 A1 | 11/2005 | de Villiers et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0025862 A1 | 2/2006 | de Villiers et al. |
| 2006/0029186 A1 | 2/2006 | de Villiers et al. |
| 2006/0030857 A1 | 2/2006 | de Villiers et al. |
| 2006/0036325 A1 | 2/2006 | Paul et al. |
| 2006/0041313 A1 | 2/2006 | Allard et al. |
| 2006/0069439 A1 | 3/2006 | Zucherman et al. |
| 2006/0178744 A1 | 8/2006 | de Villiers et al. |
| 2006/0195097 A1 | 8/2006 | Evans et al. |
| 2006/0241641 A1 | 10/2006 | Albans et al. |
| 2006/0293754 A1 | 12/2006 | de Villiers et al. |
| 2007/0061011 A1 | 3/2007 | de Villiers et al. |
| 2007/0123903 A1 | 5/2007 | Raymond et al. |
| 2007/0123904 A1 | 5/2007 | Stad et al. |
| 2007/0282449 A1 | 12/2007 | de Villiers et al. |
| 2008/0051900 A1 | 2/2008 | de Villiers et al. |
| 2008/0051901 A1 | 2/2008 | de Villiers et al. |
| 2008/0125864 A1 | 5/2008 | de Villiers et al. |
| 2008/0133011 A1 | 6/2008 | de Villiers et al. |
| 2008/0154301 A1 | 6/2008 | de Villiers et al. |
| 2008/0154382 A1 | 6/2008 | de Villiers et al. |
| 2008/0215155 A1 | 9/2008 | de Villiers et al. |
| 2008/0221696 A1 | 9/2008 | de Villiers et al. |
| 2008/0228274 A1 | 9/2008 | de Villiers et al. |
| 2008/0228277 A1 | 9/2008 | de Villiers et al. |
| 2008/0294259 A1 | 11/2008 | de Villiers et al. |
| 2009/0043391 A1 | 2/2009 | de Villiers et al. |

FOREIGN PATENT DOCUMENTS

| | | |
|---|---|---|
| EP | 0333990 A2 | 9/1989 |
| EP | 0 560 140 A1 | 9/1993 |
| EP | 0 560 141 A1 | 9/1993 |
| EP | 0560140 A1 | 9/1993 |
| EP | 0560141 A1 | 9/1993 |
| EP | 0591712 A1 | 4/1994 |
| EP | 820740 | 1/1998 |
| EP | 1142544 A1 | 10/2001 |
| EP | 1 153 582 A2 | 11/2001 |
| EP | 1153582 A2 * | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1417940 A1 | 5/2004 |
| WO | WO 99/20209 | 4/1999 |
| WO | WO 99/30651 | 6/1999 |
| WO | WO 00/35384 | 6/2000 |
| WO | WO 01/01893 A1 | 1/2001 |
| WO | WO 2004/026187 A1 | 4/2004 |
| WO | WO 2004-026187 A1 | 4/2004 |
| WO | WO 2005/053580 A1 | 6/2005 |
| WO | WO 2005/072662 | 8/2005 |

OTHER PUBLICATIONS

Hellier et al., "Wear Studies for Development of an Intervertebral Disc Prosthesis," *Spine*, vol. 17 No. 6 Supplement pp. 86-96 (1992).

Lee et al., "Impact Response of the Intervertebral Disc in a Finite-Element Model," *Spine* vol. 25, No. 19, pp. 2431-2439.

Lehuec et al., "Shock Absorption in Lumber Disc Prosthesis," *Journal of Spinal Disorders & Techniques*, vol. 16, No. 4, pp. 346-351.

* cited by examiner

US 8,685,035 B2

INTERVERTEBRAL PROSTHESIS PLACEMENT INSTRUMENT

CROSS-REFERENCES TO RELATED APPLICATIONS

This application is a continuation of International Application PCT/IB2004/000171, filed on Jan. 26, 2004, which claims priority from South African application 2003/0875, filed on Jan. 31, 2003, the full disclosures of which are incorporated herein by reference.

BACKGROUND OF THE INVENTION

This invention relates to an intervertebral prosthesis placement instrument.

Various types of intervertebral prosthesis are known. Examples are that marketed by Waldemar Link GmbH & Co under the trade mark LINK® SB Charite and those described in EP 0 560 140, EP 0 560 141 (both Waldemar Link GmbH & Co) and ZA 2002/7517.

It is an object of the present invention to provide an instrument which can be used to place an intervertebral prosthesis, such as one of those mentioned above, in an intervertebral space.

BRIEF SUMMARY OF THE INVENTION

According to the present invention there is provided an intervertebral prosthesis placement instrument comprising opposed jaws having tips shaped for insertion between adjacent vertebrae between which the prosthesis is to be placed, the jaws being movable apart from one another to cause distraction of the vertebrae and having opposing surfaces shaped to embrace the prosthesis between them and to guide the prosthesis into position between the distracted vertebrae.

In the preferred embodiment, the tips of the jaws are relatively sharp in relation to remaining portions of the jaws, thereby enabling the tips to be inserted between the vertebrae prior to distraction. The opposing surfaces of the jaws may include slots in which fins carried by the prosthesis and projecting in opposite directions are slidably receivable, the slots serving in use to guide the fins into opposing slots formed in the vertebrae.

The jaws may be carried by a scissors, forceps or tongs type mechanism having handles operable to move the jaws apart from one another. Preferably the jaws are inclined relative to one another and the handles are inclined relative to the slots, these features allowing the prosthesis to be inserted initially between the jaws.

The jaws may, for instance, inclined towards one another in a direction towards their tips with the maximum spacing between the jaws at positions remote from the tips being sufficient for the prosthesis to be inserted between the jaws.

Further according to the invention there is provided the combination of an instrument as summarized above and a tool which is operable to drive the prosthesis through the jaws and into position between the vertebrae:

Other features of the invention are set forth in the appended claims.

BRIEF DESCRIPTION OF THE DRAWINGS

The invention will now be described in more detail, by way of example only, with reference to the accompanying drawings in which.

DETAILED DESCRIPTION OF THE INVENTION

Figure 1:
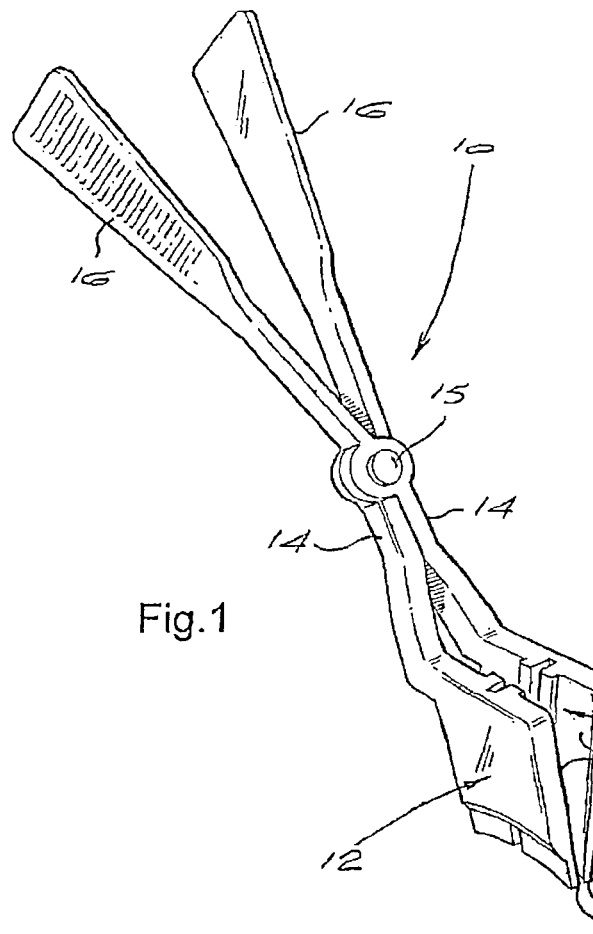
FIG. 1 shows a perspective view of an instrument according to this invention.

The illustrated intervertebral prosthesis placement instrument 10 has a pair of jaws 12 carried by arms 14 which form part of a scissor-type mechanism having a single hinge point 15 and which are provided with handles 16 at their ends remote from the jaws. The jaws have opposing surfaces 18 formed with inwardly projecting ribs 20 and transverse slots 22 which extend for the height of the jaws as viewed in FIG. 2. At their free ends the jaws 12 are provided with relatively sharp tips or blades 24 having curved extremities 26.

Figure 2:
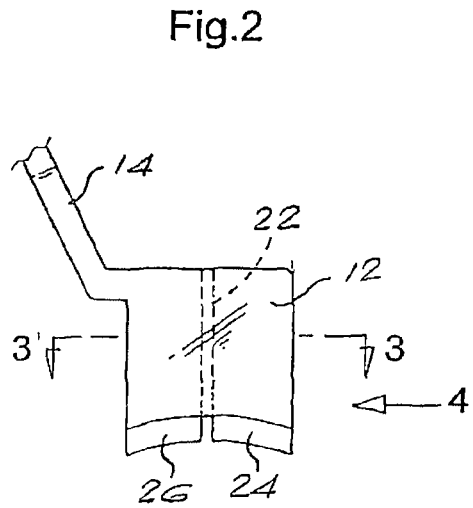
FIG. 2 shows a side view of a portion of the instrument seen in FIG. 1.
Figure 3:
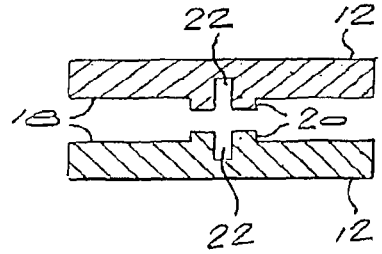
FIG. 3 shows a cross-section at the line 3-3 in FIG. 2.

As will be apparent from FIGS. 1 and 2, the arms 14 are inclined relative to the jaws. It will be understood that by appropriate manipulation of the handles 16, in the illustrated case by moving them apart from one another, will serve to pivot the jaws apart from one another. The invention also envisages embodiments in which a double hinge arrangement is provided whereby movement of the handles towards one another will pivot the jaws apart from one another.

Reference is made, by way of example only, to the specification of applicant's international patent application PCT/IB03/04051 which describes an intervertebral prosthesis having opposing plates located on opposite sides of a central core on which the plates can articulate. The plates have projecting fins which, during placement of the prosthesis, locate in slots created for the purpose in opposing surfaces of adjacent vertebra between which the prosthesis is to be installed.

The instrument illustrated in FIGS. 1 to 4 is designed for use in placement of such a prosthesis. The prosthesis is indicated in FIG. 5 by the numeral 30. The abovementioned plates are indicated by the numeral 32, the core by the numeral 34 and the fins by the numeral 36.

FIG. 5 also shows portions of two adjacent vertebra 38 in which saw cuts have been made to form the slots 40 which will receive the fins.

In order to place the prosthesis 30 it is necessary to distract the vertebra, i.e separate them by a distance sufficient for entry of the prosthesis between them. To achieve this the tips 24 of the jaws 12 are inserted between the vertebra with the slots 22 in the jaws aligned with the slots 40. The handles 14 may then be manipulated to force the jaws, and hence the vertebrae, apart from one another. The prosthesis 30 is then slipped into the gap between the jaws so as to be embraced therein with the fins 36 in the slots 22. The prosthesis is then slipped downwardly through the inter-jaw gap. Throughout this movement the prosthesis is guided by the guidance of the fins 36 in the slots 22. The prosthesis is moved right through the inter-jaw gap and eventually past the tips 24 so as to locate between the vertebrae with the fins in the slots 40.

It will accordingly be understood that the slots 22 serve to guide the fins into the slots 40.

Figure 4:
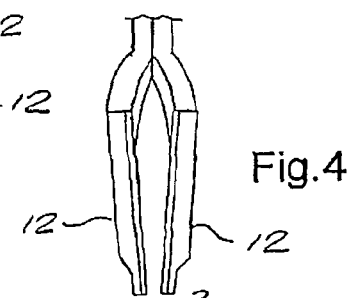
FIG. 4 shows a view of the instrument in the direction of the arrow 4 in FIG. 2.
Figure 5:
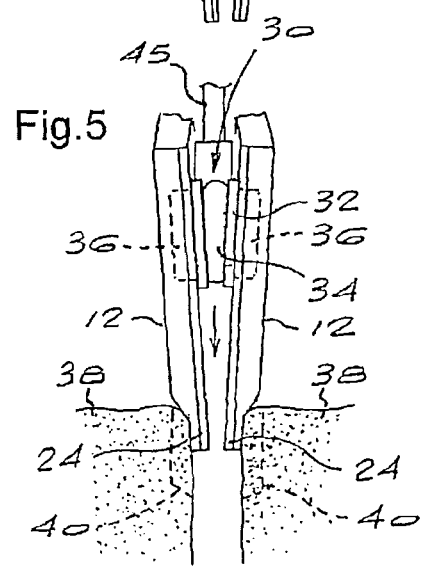
FIG. 5 shows the instrument in use.

Referring to FIG. 4 it will be noted that the jaws are inclined towards one another in a direction towards their tips 24. The gap 42 between them at the top, i.e. at their extremities remote from the tips 24, is sufficient for initial insertion of the prosthesis between them at this location. Thus in an alternative placement procedure it is possible to locate the prosthesis initially in the gap 42 and then drive it downwardly so as to force the jaws, and hence the vertebrae, apart from one another instead of manipulating the handles to force the jaws apart. The numeral 44 in FIG. 5 indicates a tool which is used to hold and position the prosthesis during the placement procedure. It will be possible to tap on the upper end of this instrument to drive the prosthesis downwardly as required.

It will also be understood that the procedures described above may be combined, so that initial distraction of the vertebra is achieved by manipulation of the handles 14 and subsequent distraction to the distance necessary to accommodate the prosthesis between them is achieved by tapping or otherwise urging the prosthesis downwardly.

The instrument 10 serves both to facilitate insertion of the prosthesis between the vertebrae and to ensure that the prosthesis is accurately guided into position so that its fins 36 locate properly in the slots 40.

What is claimed is:

1. An intervertebral prosthesis placement instrument comprising opposed jaws having tips shaped for insertion between adjacent vertebrae between which the prosthesis is to be placed, the jaws being movable apart from one another to cause distraction of the vertebrae and having opposing inner surfaces shaped to embrace the prosthesis between them and to guide the prosthesis into position between the distracted vertebrae, wherein each of the opposing surfaces of the jaws include slots therein to slidably receive fins carried by the prosthesis, the slots adapted to guide the fins into opposing slots formed in the vertebrae.

2. An instrument according to claim 1, wherein the tips of the jaws are sharpened to facilitate insertion between the adjacent vertebrae.

3. An instrument according to claim 1, wherein the opposing surfaces of the jaws are formed with inwardly projecting ribs and the slots are formed in the ribs.

4. An instrument according to claim 1, wherein the jaws are carried by a scissors-type mechanism having handles operable to move the jaws apart from one another.

5. An instrument according to claim 4, wherein the handles are inclined relative to the jaws.

6. An instrument according to claim 5, wherein the jaws are inclined relative to one another.

7. An instrument according to claim 6, wherein the jaws are inclined towards one another in a direction towards their tips, the maximum spacing between the jaws at positions remote from the tips being sufficient for the prosthesis to be inserted between the jaws.

8. A system comprising an instrument according to claim 7, and a tool operable to drive the prosthesis through the jaws and into position between the vertebrae.

9. An instrument according to claim 1, wherein the slots extend partially through the jaws.

10. An instrument according to claim 1, wherein the slots extend all the way through the jaws at a distal end of the jaws.

11. An instrument according to claim 1, wherein a portion of the slots extend partially through the jaws and a portion of the slots extend all the way through the jaws.

12. An instrument according to claim 1, wherein each of the slots is configured to receive and guide a single fin into the slots formed in the vertebrae.

13. A system for implanting an intervertebral prosthesis, the system comprising:

a prosthesis having two vertebral contacting surfaces and at least one fin extending from one of the vertebral contacting surfaces, the fin shaped to be received in a slot cut into the vertebra;

a placement instrument comprising opposed jaws having tips shaped for insertion between adjacent vertebrae between which the prosthesis is to be placed, the jaws being movable apart from one another to cause distraction of the vertebrae and having opposing inner surfaces shaped to embrace the prosthesis between them and to guide the prosthesis into position between the distracted vertebrae, at least one of the opposing inner surfaces of the jaws including at least one slot therein which is configured to slidably receive and guide the fin of the prosthesis into the slot cut into the vertebrae.

14. A system according to claim 13, wherein the at least one fin comprises a fin on each of the two vertebral contacting surfaces and the at least one slot comprises a slot on each of the opposing inner surfaces of the jaws.

15. A system according to claim 13, wherein the tips of the jaws are sharpened to facilitate insertion between the adjacent vertebrae.

16. A system according to claim 14, wherein the opposing surfaces of the jaws are formed with inwardly projecting ribs and the slots are formed in the ribs.

17. A system according to claim 13, wherein the jaws are carried by a scissors-type mechanism having handles operable to move the jaws apart from one another.

18. A system according to claim 17, wherein the handles are inclined relative to the jaws.

19. A system according to claim 17, wherein the jaws are inclined relative to one another.

20. A system according to claim 17, wherein the jaws are inclined towards one another in a direction towards their tips, the maximum spacing between the jaws at positions remote from the tips being sufficient for the prosthesis to be inserted between the jaws.

21. A system according to claim 13, further comprising an instrument a tool operable to drive the prosthesis through the jaws and into position between the vertebrae.

22. A system according to claim 13, wherein the at least one slot is configured to receive and guide a single fin into the slot formed in the vertebrae.

23. A system according to claim 13, wherein the at least one fin is in the form of an elongated member which is elongated in a direction of insertion.

24. A system according to claim 13, wherein the prosthesis is an articulating intervertebral disc.

25. An intervertebral prosthesis placement instrument comprising opposed jaws having tips shaped for insertion between adjacent vertebrae between which the prosthesis is to be placed, the jaws being movable apart from one another to cause distraction of the vertebrae and having opposing inner surfaces shaped to embrace the prosthesis between them and to guide the prosthesis into position between the distracted vertebrae, wherein each of the opposing surfaces of the jaws include a narrow slot therein configured to slidably receive a single fin carried by the prosthesis, the slots adapted to guide the fins into corresponding slots formed in the vertebrae.

26. An instrument according to claim 25 in combination with an intervertebral prosthesis in the form of an articulating artificial disc.

* * * * *